US00PP09000P

United States Patent [19]

Meilland

[11] Patent Number: Plant 9,000

[45] Date of Patent: Dec. 6, 1994

[54] MINIATURE ROSE PLANT NAMED MEIMAGUL

[75] Inventor: Alain A. Meilland, Antibes, France

[73] Assignee: The Conard-Pyle Company, West Grove, Pa.

[21] Appl. No.: 161,468

[22] Filed: Dec. 6, 1993

[51] Int. Cl.[5] ..... A01H 5/00
[52] U.S. Cl. ..... Plt./7.1
[58] Field of Search ..... Plt. 7.1, 10

*Primary Examiner*—Howard J. Locker

*Attorney, Agent, or Firm*—Burns, Doane, Swecker & Mathis

[57] ABSTRACT

A new and distinct variety of rose plant of the Miniature Class is provided which abundantly forms attractive bicolored double blossoms which exhibit a generally velvet red appearance with some yellow coloration when viewed from above. The plant is bushy, and forms very vigorous vegetation that is dense and semi-dull in appearance. The blossoms possess no fragrance. The plant is well adapted to pot forcing under light, and grows well on its own roots. The foliage is medium green in coloration and tends to be well-pointed.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the product of the pollination of the Bonfire Night variety (non-patented in the United States) by the Meialfi variety (U.S. Plant Pat. No. 2,140). The Meialfi variety sometimes is known as the Zambra variety. The male parent (i.e., the pollen parent) of the new variety was the RUGUL variety (non-patented in the United States). The parentage of the new variety can be summarized as follows:

(BONFIRE NIGHT×MEIALFI)×RUGUL.

The seeds resulting from the above pollination were sown and 301 plantlets were obtained which were physically and biologically different from each other. Selective study resulted in the identification of a single plant of the new variety.

It was found that the new variety of Miniature rose plant of the present invention possesses the following combination of characteristics:

(a) forms in abundance attractive double bicolored blossoms which exhibit a generally velvet red appearance with some yellow coloration when viewed from above,
(b) forms medium-green pointed foliage,
(c) exhibits a bushy growth habit,
(d) is well adapted to pot forcing under light, and
(e) grows well on its own roots.

The new variety well meets the needs of the horticultural industry. It is particularly well-suited for use as attractive ornamentation in the landscape.

The new variety has been found to undergo asexual propagation in France by a number of routes, including budding, grafting, cuttage. Asexual propagation by cuttings as performed in France has shown that the characteristics of the new variety are strictly transmissible from one generation to another.

The new variety has been named the Meimagul variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were two years of age and were observed during September while growing on their own roots indoors at LeCannet des Maures, Var, France.

FIG. 1 — illustrates a specimen of a young shoot;

FIG. 2 — illustrates specimens of two floral buds before the opening of the sepals;

FIG. 3 — illustrates specimens of two floral buds at the opening of the sepals;

FIG. 4 — illustrates specimens of two floral buds at the opening of the petals;

FIG. 5 — illustrates specimens of two flowers during the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates specimens of leaves with three leaflets with the upper surface being shown at the right and the under surface being shown at the left;

FIG. 15 — illustrates specimens of leaves with five leaflets with the upper surface being shown at the left and the under surface being shown at the right; and FIG. 16 — illustrates specimens of leaves with seven leaflets with the upper surface being shown at the left and the under surface being shown at the right.

DETAILED DESCRIPTION

Figures 1, 2, 3, 4, 5, 6, 7, 8, 9, 10, 11, 12, 13, 14, 15, 16:
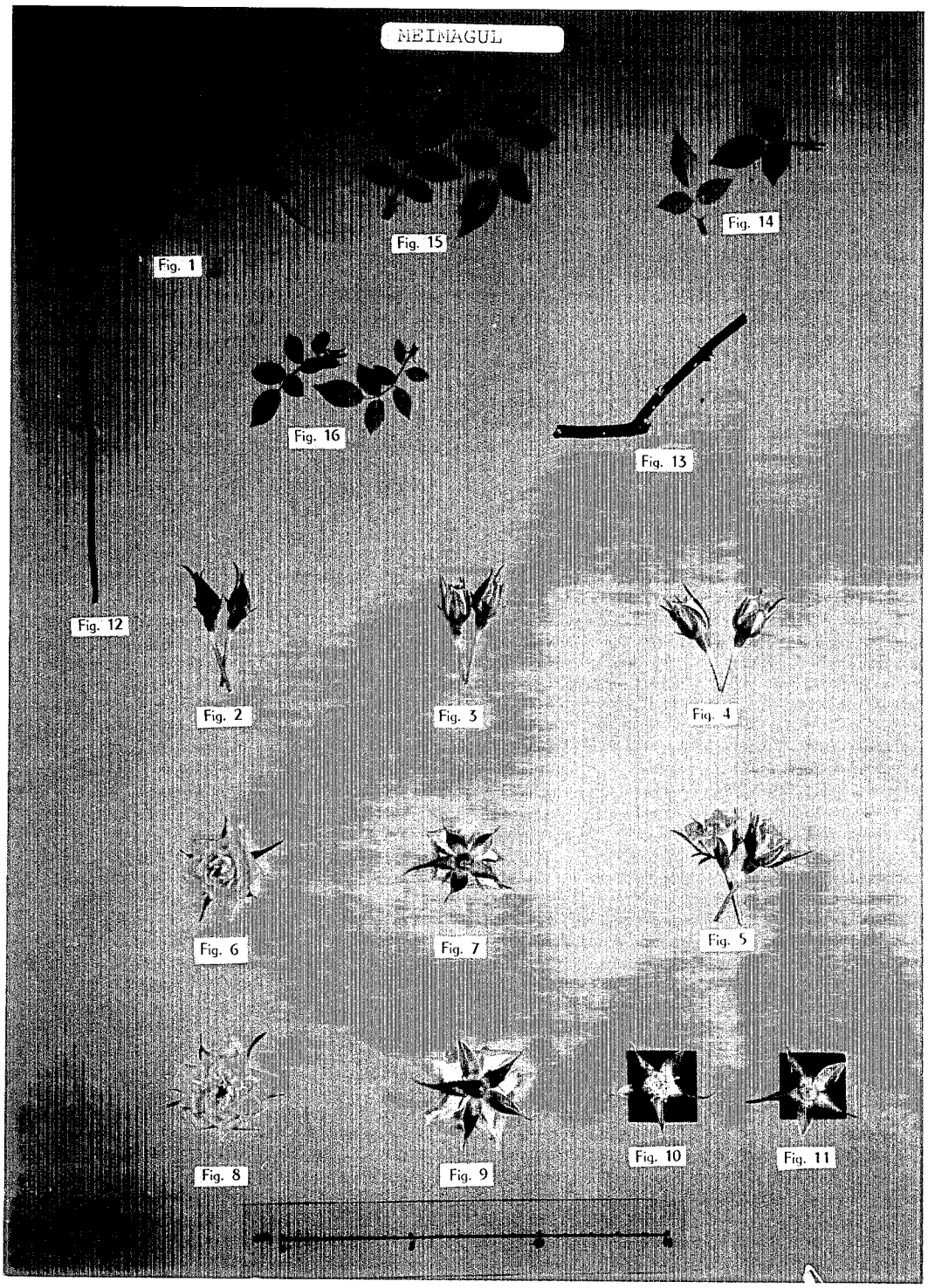

The chart used in the identification of the colors is that of The Royal Horticultural Society (R.H.S. Colour Chart). The terminology which precedes reference to the chart has been added to indicate the corresponding colors in more common terms. The description is based on two year-old specimens of the new variety which were observed during September while growing on their own roots indoors at LeCannet des Maures, Var, France.

Class: Miniature.

Plant:

*Height.*—Approximately 25 cm. on average at the end of the growing season. Flower stem lengths of approximately 5 to 8 cm. commonly are formed.

*Habit.*—Bushy.

Branches:

*Color.*—Young stems: light green, Green Group 143B. Adult wood: medium green, Green Group 137B.

*Thorns.*—Size: small. Quantity: few. Color: greenish coloration on young and adult stems.

Leaves:

*Petioles.*—Upper surface: striped, reddish brown on young foliage and medium green on mature foliage with glandular edges. Under surface: light green with a few thorns.

*Stipules.*—Adnate, pectinate, narrow and linear.

*Leaflets.*—Number: 3, 5 (most often), and 7 Shape: lanceolate. Serration: simple and regular. Texture: consistent. General appearance: very dense and semi-dull foliage. Color (young foliage): upper surface: light green, Green Group 143C. under surface: light green, Green Group 143D, and slightly suffused with reddish coloration. Color (adult foliage): upper surface: light green, Green Group 143B. under surface: light green, Green Group 143C.

Inflorescence:

*Number of flowers.*—Approximately 1 to 3 per stem.

*Peduncle.*—Light green, long, bears small glandular prickles, and its length is approximately 3 to 3.5 cm. on average.

*Sepals.*—Upper surface: tomentose and greenish in coloration. under surface: not very glandular and is appendiculated.

*Buds.*—Shape: conical. Length: approximately 1.5 cm. on average. Size: medium for this class. Color upon opening: upper surface: Current Red, Red Group 46B, with a central yellow vein on central petals, and Light Sulfur Yellow, Yellow Group 6D at the base. under surface: Sulfur Yellow, Yellow Group 6D, and widely edges and spotted with Cardinal Red, Red Group 53B.

*Flower.*—Form: cupped at opening and changing to an umbrella configuration when more fully open. Diameter: approximately 3.5 to 4 cm. on average. Color (when opening begins): upper surface: Strawberry Red, Red Group 46B, with a central yellow vein on central petals, and Light Sulfur Yellow, Yellow Group 6D at the base. There is a generally velvet red appearance with some yellow coloration when viewed from above. under surface: Sulfur Yellow, Yellow Group 6D, and widely edged and spotted with Cardinal Red, Red Group 53B. Color (when blooming): upper surface: Strawberry Red, Red Group 46B, with a central yellow vein on central petals, and Light Sulfur Yellow, Yellow Group 6D at the base. There is a generally velvet red appearance with some yellow coloration when viewed from above. under surface: Sulfur Yellow, Yellow Group 6D, and widely edged and spotted with Cardinal Red, Red Group 53B. Color (at end of blooming): upper surface: Strawberry Red, Red Group 46B, with a central yellow vein on the innermost petals, and Light Sulfur Yellow, Yellow Group 6D at the base. There is a generally velvet red appearance with some yellow coloration when viewed from above. under surface: Sulfur Yellow, Yellow Group 6D, and widely edged and spotted with Cardinal Red, Red Group 53B. Fragrance: none. Lasting quality: very long when on the plant. The flowers commonly last approximately two weeks or longer in the spring and approximately one week or longer in the summer when the days are warmer. Petal number: approximately 51 to 68 on average. Petal shape: oval with reflexed edges and commonly with the presence of some fringed edges at the center of the flower. Petal drop: good. Anthers: normal and golden yellow in coloration. Stamen number: approximately 25 to 29 on average. Filaments: greenish in coloration. Pistil number: approximately 22 to 28 on average. Stigmas: normal. Styles: fuchsia in coloration, greenish near the base, and of irregular heights. Receptacle: light green, smooth, and in longitudinal section in the shape of a pitcher.

Development:

*Vegetation.*—Very vigorous.

*Blooming.*—Very abundant.

*Aptitude to bear fruit.*—Good.

*Resistance to diseases.*—Good.

I claim:

1. A new and distinct variety of Miniature rose plant characterized by the following combination of characteristics:

(a) forms in abundance attractive double bicolored blossoms which exhibit a generally velvet red appearance with some yellow coloration when viewed from above,
(b) forms medium-green pointed foliage,
(c) exhibits a bushy growth habit,
(d) is well adapted to pot forcing under light, and
(e) grows well on its own roots;

substantially as herein shown and described.

* * * * *

MEIMAGUL